United States Patent [19]

Baker et al.

[11] Patent Number: 4,666,638
[45] Date of Patent: May 19, 1987

[54] FRAGRANCE DEVICE

[75] Inventors: Richard I. Baker, Newtown; Richard J. Wegrzyn, Stratford; Edward Szymansky, Fairfield, all of Conn.

[73] Assignee: Remington Products, Inc., Bridgeport, Conn.

[21] Appl. No.: 769,932

[22] Filed: Aug. 27, 1985

[51] Int. Cl.$^4$ .............................................. B01F 3/04
[52] U.S. Cl. .............................. 261/26; 261/DIG. 65; 239/57; 315/159
[58] Field of Search ............... 315/159; 261/DIG. 65, 261/26, 30; 250/239; 239/57

[56] References Cited

U.S. PATENT DOCUMENTS

| | | | |
|---|---|---|---|
| 1,131,307 | 3/1915 | Wunschow | 261/30 |
| 2,351,267 | 6/1944 | Irwin | 239/57 |
| 2,734,769 | 2/1956 | Holz | 239/57 |
| 3,087,679 | 4/1963 | Wilson | 239/57 |
| 3,128,413 | 4/1964 | Person | 250/239 |
| 3,475,617 | 10/1969 | Chaimowicz | 250/239 |
| 3,902,877 | 9/1975 | Swaim | 55/279 |
| 3,993,444 | 11/1976 | Brown | 261/DIG. 65 |
| 4,023,035 | 5/1977 | Rodriguez | 315/159 |
| 4,339,079 | 7/1982 | Sato et al. | 239/57 |
| 4,383,951 | 5/1983 | Palson | 261/DIG. 65 |

Primary Examiner—Tim Miles

[57] ABSTRACT

A light responsive, battery operated fragrance device is described. The device establishes an air stream over a fragrant material when an artificial light source such as a room lamp is energized. It includes a swivel light gathering body and a photo transistor mounted thereto which can be aimed at the artificial light source and provides directional discrimination and screening of other light sources. The unactuated device provides a limited flow of convection air current which maintains a relatively low level of fragrance dispersion in a room therefor. Upon actuation forced air flowing through the device causes a rapid increase in the level of fragrance dispersion in the room.

21 Claims, 10 Drawing Figures

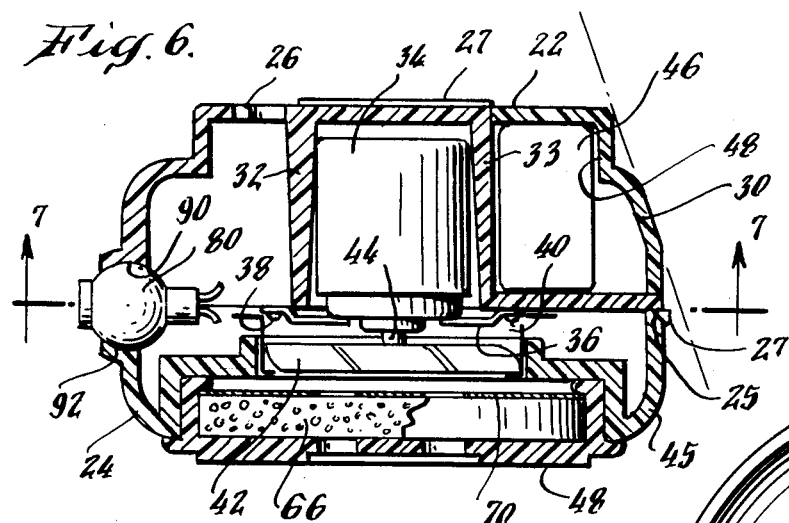
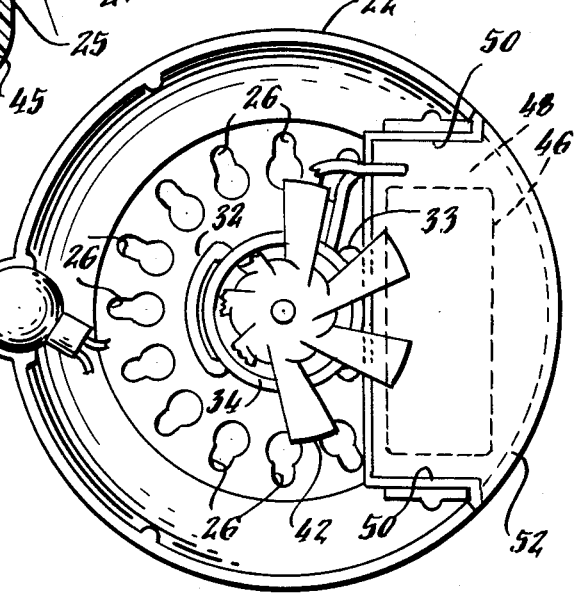
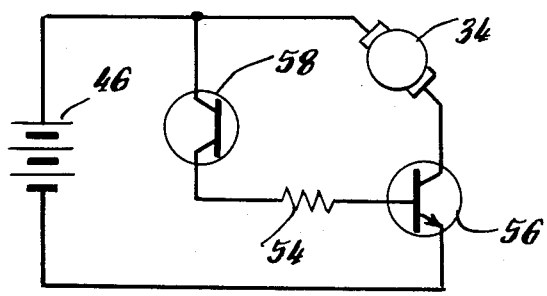
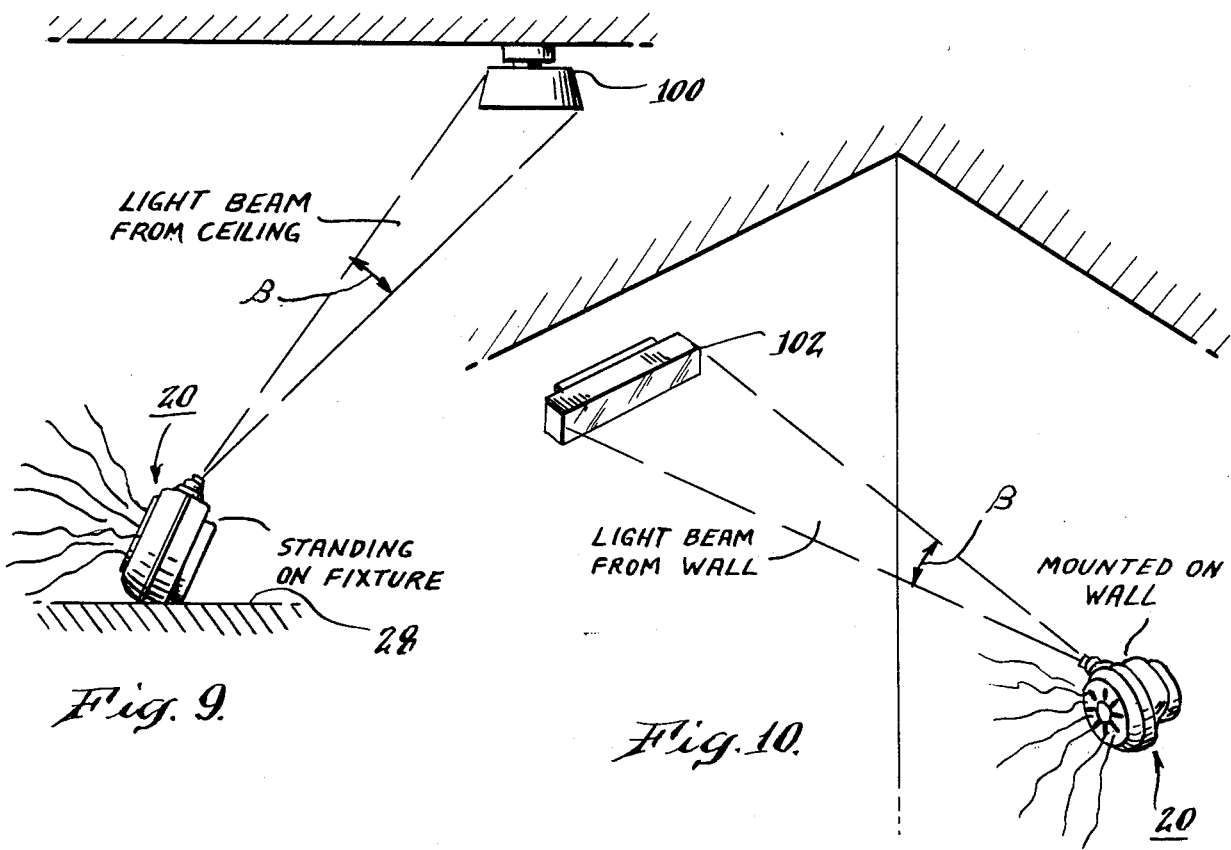

FRAGRANCE DEVICE

BACKGROUND OF THE INVENTION

1. Field of the Invention

This invention relates to devices which automatically discharge a fragrance into an enclosed area. The invention relates more particularly to an improved form of fragrance device which is actuated by an artificial light source.

2. Description of the Prior Art

Devices are known in the art which are adapted to discharge fragrances into an enclosed area. These devices comprise a housing containing a material which emits a fragrance and a means for flowing air over the fragrant material. In a convection air current arrangement, the housing is apertured and room convection currents flow through the device and carry the fragrance to the room. In a powered fan form of device, an electric motor and fan in the housing cause air to flow over the device and establish an air stream through the device. In the latter case, a source of electric power must be provided and a switching means is required to enable selective application of power to the device. A service voltage is used as a source of electrical power in one form of powered fan device. The application of electric power is selectively supplied to the device and is interrupted as the need arises. Electrical wire connections between the service voltage and device limit placement of the device in a room and detracts from its appearance. Moreover, a failure to manually turn off the device results in over scenting of the area and rapid depletion of the fragrant material thus necesitating frequent maintenance and increasing the cost of operating the device. While battery operated devices obviate the need for electrical wire coupling between the source and the device, the batteries must supply the relatively heavy current requirements of an electric motor and are thus subject to rapid depletion unless the device is consistently turned on and off. Each of the foregoing arrangements suffers further from the continuous delivery of a fragrance into the room when the room may not be in use, a form of operation which is relatively wasteful and inefficient and results in overscenting of the room and rapid depletion of the fragrant material.

In an attempt to correct some of these deficiencies, it has been proposed to condition the operation of the device on the energization of an artificial light source in the area. By this technique, the device is actuated when an artificial light source in the area is energized. This will be the case, for example, in a bathroom in which a person entering switches on and energizes an overhead or wall lamp. As the lamp is energized, the fragrance device detects the artificial light and causes a forced flow discharge of the fragrance into the room. A known form of device has utilized solar cells which derive energy from the light of an artificial light source for operating a motor of the device. However, the state of the art of present day solar cells is such that the solar cells must be mounted directly to the light fixture itself in order to capture sufficient light energy to generate electrical energy for operating the fan motor. This is often cumbersome and necessitates modification of the fixture itself. In addition, unless the housing of the fragrance device is mounted to the light fixture, then an electrical wire coupling is required between the solar cells and the device, a requirement which limits placement of the device in a room and detracts from its appearance. Moreover, solar cells also respond to ambient sunlight, they continuously supply an output voltage, and they require a voltage control circuit to avoid actuating the device when not selectively enabled.

In addition to the foregoing disadvantages of prior art fragrance devices, these arrangements have exhibited a tendancy to quickly deplete the fragrance material, simply as a result of the continuous flow of convection currents through the device. Of necessity, an air flow path must be provided in the device in order that air may flow over the fragment material and carry the scent from the device into the room. But convection currents deplete the material more rapidly than is desired and frequent maintenance is necessitated. In addition, those fragrance devices which are actuated by the energization of an artificial light source may exhibit erratic operation in rooms which are also exposed both to artificial light and to natural daylight, such as would occur with a room having a window. In battery operated devices which respond to energization of an artificial light source, it is necessary to carefully adjust the sensitivity since the device can be activated at relatively low light levels, such as may be produced by ambient light thus resulting in undesired energization of the device and rapid depletion of the fragrance material.

SUMMARY OF THE INVENTION

Accordingly, it is an object of this invention to provide an improved, battery operated fragrance device which is actuated upon the energization of an artificial light source and which is deactivated upon interruption of the artificial light source.

Another object of the invention is to provide an improved light actuated fragrance device having direction selectivity to light sources.

Another object of the invention is to provide an improved fragrance device which is actuated by an artificial light source.

Another object of the invention is to provide for a rapidly increased, controlled level of fragrance dispersion upon actuation of the device.

A further object of the invention is to provide a fragrance device having an air stream flow path which reduces convection current through the device and extends the life of the fragrant material.

Another object of the invention is to provide a light acutated fragrance device which extends the life of a battery which energizes a motor of the device.

Another object of the invention is to provide a light actuated fragrance device which may be placed conveniently in a room without restricting connecting wires and the like.

Still another object of the invention is to provide an improved device of the type described which can be operated alternatively in a free standing attitude or from a wall mounted position.

In accordance with the invention, an improved fragrance device comprises a housing, a light responsive electrically energized means which establishes an air stream through the housing, a fragrance means positioned in the housing in the air stream and a light capturing body positioned on the housing. The light capturing body is mounted to provide for manual adjustment thereof and enabling aiming of the body at a source of illumination whereby the electrically energized means becomes energized upon the capture by the body of light from the illumination source. In a preferred embodiment, the electrically energized means is battery operated. In accordance with other features of the invention, directional selectivity and sensitivity is provided by adjustably positioning a light sensitive means in the body.

In accordance with other features of the invention, air flow apertures enabling air to flow to the interior of the housing are provided and are arranged for restricting the flow of convection currents therethrough to a low level relative to the flow of forced air. Upon actuation of the device, the flow of forced air rapidly increases the dispersion of fragrance in a room.

BRIEF DESCRIPTION OF THE DRAWINGS

These and other features and objects of the invention will become apparent with reference to the following specification and to the drawings wherein:

FIG. 6 is a view taken generally along line 6—6 of FIG. 2;

FIG. 7 is a view taken along line 7—7 of FIG. 6 which illustrates aiming of the light capturing body;

FIG. 8 is a schematic diagram of a circuit arrangement used with the device of FIG. 1;

FIG. 9 is a diagram illustrating use of the device of FIG. 1 in a free standing attitude; and, FIG. 10 is a diagram illustrating use of the device of FIG. 1 when it is mounted to a vertical support structure.

DETAILED DESCRIPTION

Figure 1:
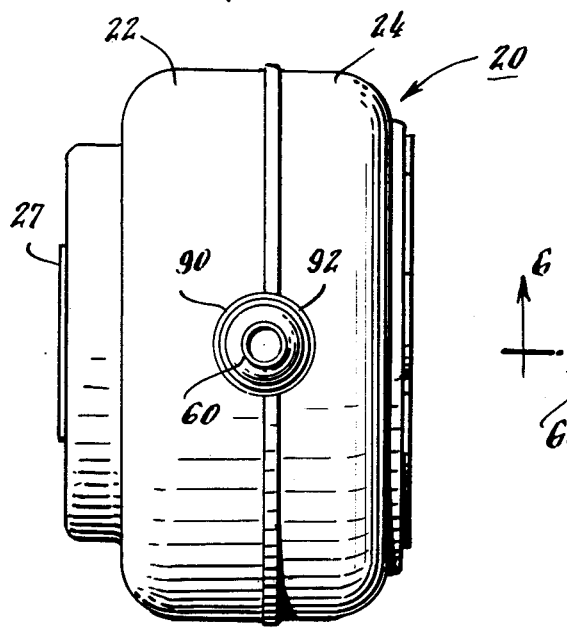
FIG. 1 is a side elevation view of a fragrance device constructed in accordance with features of this invention.
Figure 2:
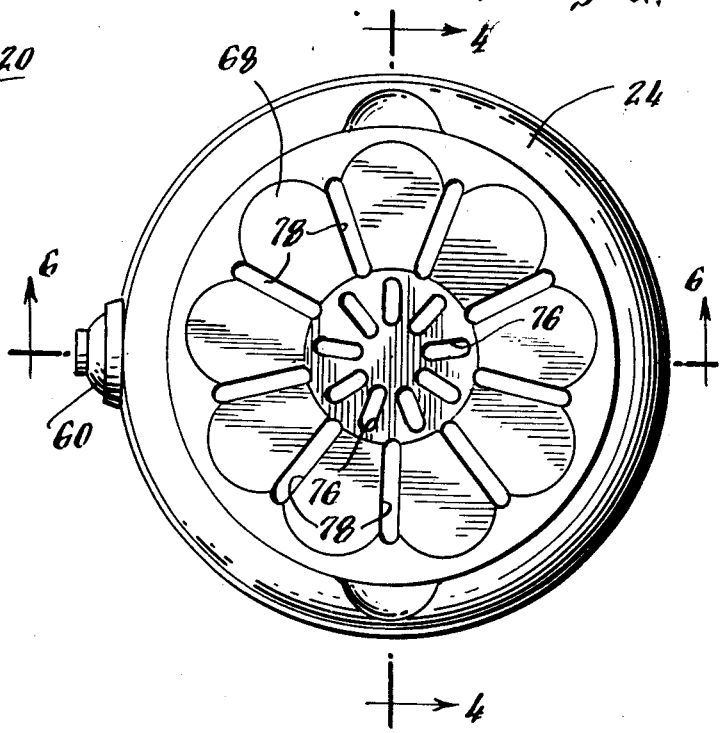
FIG. 2 is a front elevation view of the device of FIG. 1.
Figure 3:
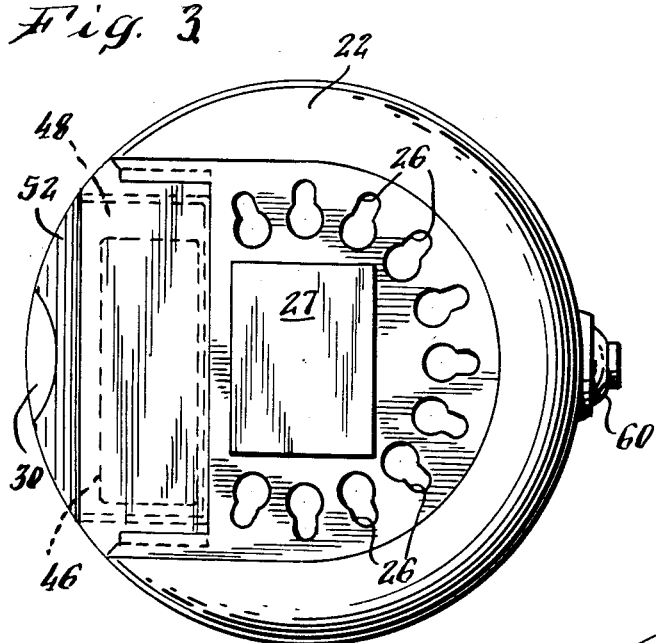
FIG. 3 is a rear elevation view of the device of FIG. 1, in which an interior battery compartment is shown in dotted lines.
Figure 4:
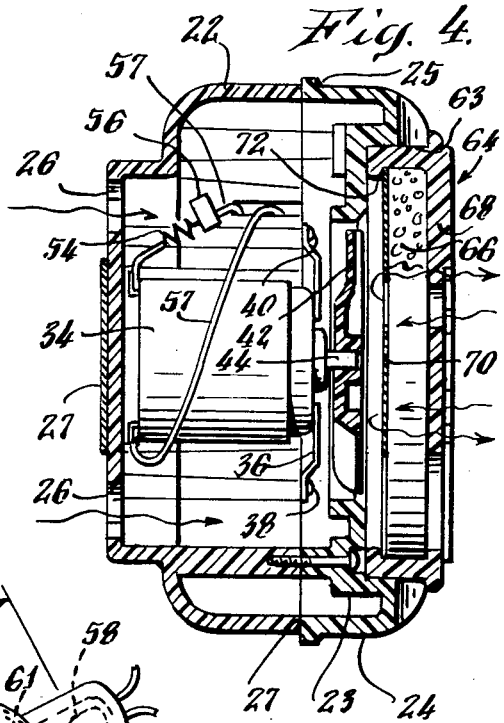
FIG. 4 is a view taken along line 4—4 of FIG. 2.

Referring now to the drawings, the fragrance device is shown to have a housing 20 which is formed of a generally bowl-shaped base member 22, and, a generally bowl-shaped top member 24. These members are formed of a polymer plastic such as a styrene and are secured in fixed assembly by any suitable means such as by screws 23 (FIG. 4), by ultrasonic welding, or by a solvent bond at engaging surfaces 25 and 27 (FIG. 4). The housing 20 is adapted to be free standing as illustrated in FIG. 9 or to be supported from a vertical structure such as a wall as illustrated in FIG. 10. Base member 22 includes a semicircular array of support slots 26 for receiving a supporting screw or nail. Base member 22 may also be supported on a vertical surface by an adhesive tape 27. The device when used in a free standing position on a surface 28 as shown in FIG. 9 is positioned, on an anti-roll chamfered segment 30 (FIG. 3) formed in a curved surface of the base member. Segment 30 inhibits rolling of the housing and facilitates free standing placement on the surface 28 in the indicated attitude.

In the interior of the housing 20, base member 22 includes integrally formed longitudinally extending posts 32 and 33 for receiving and positioning an electric motor 34 within the housing. Motor 34 is captivated between segments 32 and 33 by a retainer strap 36 which is mounted to the posts by screws 38 and 40 respectively. A fan blade 42 is press fitted to an armature output shaft 44 of the motor 34 for rotation therewith. A fan blade shroud 45 is integrally formed with the top member 24.

Electrical energy for energizing the motor 34 is provided by a battery 46 which is positioned in a compartment 48 formed by wall segments 50 of the base member 22. A demountable door 52 having an outer surface conforming to the curvature of the bowl shaped base member 22 provides access to the battery compartment 48. Circuit components comprising a resistor 54 and a switching transistor 56 are coupled to and supported by wiring 57 and are coupled in a circuit arrangement, illustrated schematically in FIG. 8, with the battery 46 and with a photo transistor 58. Photo transistor 58 is positioned in a back sleeve 61 (FIG. 5) which is positioned in a bore 59 of the light capturing body 60. Alternatively, the circuit elements may be mounted to a circuit board, not shown, which is mounted in the housing at any convenient location. As described in further detail hereinafter, light actuates the photo transistor 58 and enables the application of electrical energy from the battery 46 to the motor 34.

Positioned in an aperture 63 of the top member 24 opposite the fan blade 42 is a demountable cartridge 64 of fragrant pellets 66. The cartridge 64 comprises a circular shaped top member 68, a disk shaped back member 70, and a plurality of fragrant pellets 66 which are sandwiched between the top and back members. Pellets 66 comprise, for example, pellets formed of low density polyethylene which contains a fragrant oil. Alternatively, the pellets may be formed of high density polyethylene, polypropylene or ethylene vinyl acetate. Suitable fragrant pellets are available commercially under the trademark POLYIFF from International Flavors and Fragrances of Union Beach, N.J. About 10 to 12 grams of pellets provide suitable operation for a cartridge size of about 3 inches diameter and about ½ inch thickness. A ridge 72 which is integrally formed with the top member 68 retains the back member 70 in place and the pellets 66 are thus captivated between these members. Formed in a wall segment of the top member 68 is a first, inner array of radially extending air flow slots 76, and, a second, outer array of radially extending air flow slots 78. Similarly, the back member 70 includes an inner array of radially extending air flow slots, not shown, and a secound, outer array of radially extending air flow slots, not shown. The fan blade 42, during it rotation, creates an area of relatively low pressure near its hub and an air discharge of relatively higher pressure at locations radially outward from the hub on the blades. Air is drawn into the housing through the inner array of slots in the top member, about the pellets 66, through the inner array of slots in the back member, and, also through the slots 26 formed in the base member 22. Air flowing in this stream is discharged from the interior of the housing, flowing through the outer array of slots in the back member 70, again about the pellets 66, and through the outer array of slots in the top member 68. The cartridge pellets are thus positioned in the air stream of the device. Air which is drawn into the housing from without through the cartridge flows about the pellets twice, once on intake and once on discharge. The arrows in FIG. 4 illustrates this flow.

Figure 5:
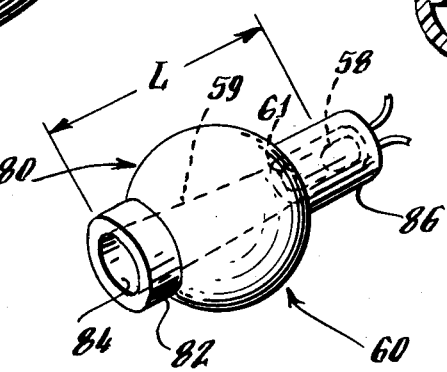
FIG. 5 is an enlarged, perspective view of the light capturing body of FIG. 1.

The light capturing body 60 is supported by the housing and is adapted to be rotated to various, different orientations in two mutually perpendicular directions, X and Y, as illustrated in FIG. 5. The body has a generally spherically shaped segment 80, a cylindrically shaped light inlet segment 82 having a light inlet aperture 84 and a rearward post segment 86. The inwardly tapering bore 59 extends through the segment 82, the spherical segment 80 and through the post segment 86. As indicated hereinbefore, the photo transistor 58 is positioned in a black sleeve 61 which is positioned in the bore 59 of the post segment 86. It is secured in the bore by an adhesive, by friction fit or by other suitable means. The photo transistor 58 is spaced from the inlet aperture 84 by a distance L. Directional selectivity of the device is increased by increasing the distance L and is decreased by decreasing the distance L. In the former case, gresater shielding of the photo transistor to light occurs while lesser shielding occurs as the photo transistor is placed closer to the light inlet aperture 84.

The housing members 22 and 24 each include a spherically shaped segment 90 and 92 which, upon assembly of members 22 and 24, together provide a socket seat for the body 80 which conforms with the spherical configuration of the segment. The body segment 80 and the surfaces 90 and 92 are configured and sized for providing that upon assembly of the body segment 80 with these housing members, a manually adjustable friction fit is established between the segment 80 and the housing members. The assembly thus resembles a ball and socket configuration wherein the segment 80 is manually rotated to different orientations and retains an adjusted orientation as a result of the frictional fit.

As illustrated in FIG. 8, the photo transistor 58 is coupled in the base circuit of a switching transistor 56. When the intensity of light impinging on the photo transistor 58 is relatively low, the switching transistor 56, which is coupled in a series circuit arrangement with the battery 46 and the motor 34, maintains the motor deenergized. As the light intensity impinging on the photo transistor 58 increases, the base current to the switching transistor increases until, at a pre-determined light intensity, the base current will be sufficiently high to cause transistor 56 to switch into a conducting state. Upon conduction of the transistor 56, current flows in the motor 34 thereby energizing it and causing rotation of the fan and thus causing a discharge of fragrant air from the device 20. As the light intensity decreases, the base current to the switching transistor 56 will decrease and at a predetermined light level, the base current will be sufficiently low so as to cause the switching transistor 56 to switch into a non-conductive state. Current flow to the motor 34 and energization of the motor is interrupted thus terminating discharge of the fragrance to the room. Phototransistor 58 is responsive to light in the infra red part of the light spectrum and is thus more responsive to incandescent artificial light sources than to fluorescent sources.

The light gathering body 60 and the photo transistor 58 mounted therein provide directional selectively to sources of light which cause energization of the motor. More particularly, the body 60 may be aimed at a source of artificial light such as the light sources 100 and 102 in FIGS. 9 and 10, respectively. Energization of the device will occur within the angle $\beta$. This angle can be increased by decreasing the distance L (FIG. 5) and is decreased by increasing the distance L for a particular size of bore 59. The device thus screens out ambient, natural light as well as other artificial light sources. It can thus be made subject to control by a desired artificial light source. In addition, because of the light screening provided by the body 80, the current level prior to switching of the transistor 56 is substantially reduced thus extending the life of the battery.

The useful life of the fragrant pellets is increased by the established air flow paths and the intervals between replacement are increased. Convection current can leak into the interior of the device through the rear surface apertures 26 and through the apertures in the top member 68 of the cartridge. When the device has not been actuated by an artificial light source, convection current flow is restricted by the relative size of the openings in the cartridge top member 68 and in the back member 70. This flow is substantially further reduced when the device is wall mounted. Moreover, convection current flow through the cartridge is also impeded and substantially reduced by the flow resistance to convection current presented by the pellets. On the other hand, when the device is actuated, a relatively high level dispersion of fragrance rapidly occurs. The flow resistance to forced air in a forward direction through the cartridge is reduced by providing the cartridge top member 68 with an aperture array having a relatively larger overall surface area opening than the overall opening presented by the aperture array in the back member 70. The smaller opening in the rear member aids in the restricting convection air current in a forward direction. During periods when the device is not actuated, fragrant oil migrates toward the surface of the polymer plastic pellet material to provide a concentration of fragrant oil near the pellet's surface. Upon actuation of the device, a relatively large concentration of fragrant oil molecules are available to be conveyed in the forced air stream from the cartridge to the room. The continuous flow of forced air reduces this concentration but during a successive period when the device is not actuated, the concentration of fragrant oil at the surface of the pellets is automatically replenished. Thus, during periods of non actuation, the dispersion of fragrance is substantially limited which is desirable since nonactuation indicates that an artificial light source is not in use and the room is unoccupied. When a person enters the room and actuates an artificial light source, the dispersion of fragrance into the room is rapidly increased. The device, in addition to extending the life of the pellets by limiting convection current flow, also provides greater control of the fragrance discharged by the forced air flow with resulting personal comfort.

In an exemplary arrangement not deemed limiting in any respect, the cartridge has a diameter of about 3 inches and a width of about 0.5 inch. The cartridge top member 68 has an overall surface opening of about 0.87 square inches and the member 70 has an overall opening of about 0.68 square inches. The pellets comprise POLYIFF low density polyethylene containing any suitable fragrance oil. Each pellet has a surface area of about 0.085 square inches. Preferably about 10 to about 12 grams of the pellets (about 301 to about 361 pellets) are contained in the cartridge to provide a total pellet surface of about 25.81 square inches to about 30.96 square inches. The fan had a diameter of about 1.75 inches and operates at about 1600 RPM.

An improved light responsive device has thus been described which exhibits enhanced directional sensitivity, reduces electrical power use, provides for injecting a blast of fragrance into a room, extends the useful life of the fragrant pellets and facilitates placement of the device in a room.

While there has been described herein a preferred embodiment of the invention, it will be appreciated that variations may be made thereto by those skilled in the art without departing from the spirit of the invention and the scope of the appended claims.

What is claimed is:

1. An improved fragrance device, comprising:
   a. A housing;
   b. An electrically energized means which is responsive to incident light for establishing an air stream through said housing;
   c. A fragrance means positioned in said housing in said air stream;
   d. A light capturing body positioned on said housing; and,
   e. Means mounting said light capturing body for providing manual adjustment of said body in two mutually perpendicular planes for enabling aiming said body at a source of artificial light whereby said electrical means is energized upon the capture of light from said light source.

2. The fragrance device of claim 1 wherein said housing includes means for supporting said housing on a vertical structure in an area in which there is located a source of artificial light and said light capturing body is manually adjustable for aiming said body at said source of artificial light.

3. The improved fragrance device of claim 2 wherein said artificial light source is electrically energized and said electrically energized means of said fragrance device is energized responsive to incident light from said light source upon energization of said electrical light source.

4. The improved fragrance device of claim 1 including a photo conductive device positioned within said light capturing body and said body and device are adapted for providing directional selectivity with respect to different sources of artificial light.

5. The improved fragrance device of claim 4 wherein said light capturing body includes a channel formed therein having an inlet aperture for capturing light incident on said body, said photo conductive device is positioned within said channel and is spaced within said channel from said inlet aperture by a distance L, and said directional selectivity is adjustable by varying the distance L.

6. An improved fragrance device, comprising:
   a. A housing;
   b. An electrically energized means, responsive to incident light, for establishing an air stream through said housing;
   c. A fragrance emitting means positioned in said air stream;
   d. Said electrically energized means including a battery, an electric motor, and a control circuit means for coupling the battery to the motor, said control circuit means including a photo-conductive device;
   e. A light capturing body for aiming at and capturing light from an artificial light source and for directing said captured light at said photo conductive device for energizing said motor; and,
   f. Means mounting said light capturing body to said housing for manual adjustment of said light capturing body in at least two mutually perpendicular planes.

7. The improved fragrance device of claim 6 wherein said photo conductive body is mounted to said light capturing body for movement therewith.

8. The improved fragrance device of claim 7 wherein said light capturing body includes a light channel formed therein, an inlet aperture for said light channel and said photo conductive device is positioned in said light channel.

9. The improved fragrance device of claim 8 wherein said light capturing body is configured for selectively capturing light from an artifical light source of limited dimensions and for screening out extraneous light.

10. An improved forced air fragrance device adapted to limit convection flow through the device, comprising:
    a. A housing;
    b. Said housing having a base member and a top member;
    c. Said top member having an aperture formed therein and supporting a fragrance cartridge which forms an apertured closure for said device;
    d. Said cartridge having an inner top member, an outer back member and a plurality of fragrant pellets contained therein;
    e. Said cartridge top and back members each having apertures formed therein to provide for both convection and forced air flow through said cartridge;
    f. Said housing including air leakage inlets through which air flows by convection into said housing and flows through said cartridge to the exterior of said housing;
    g. Said outer cartridge top member apertures providing a greater surface area opening than said inner cartridge back member apertures; and,
    h. An electrically energized means for establishing a forced air stream flowing inwardly through said cartridge apertures into said housing and then outwardly through the cartridge apertures from said housing.

11. The fragrance device of claim 10 wherein said apertures in said cartridge top and back members each comprise an inner array of radial extending air flow slots and an outer array of radial extending air flow slots.

12. The fragrance device of claim 11 wherein said cartridge is generally circular shaped.

13. A fragrance cartridge adapted for use with a forced air fragrance device which limits convection flow therethrough, comprising:
    a. A top member;
    b. A back member;
    c. Said top and back members configured to form a cartridge which provides an apertured closure for an aperture in a housing of the fragrance device;
    d. Said top and back members each having apertures formed therein to provide for forced air flow through said cartridge;
    e. Said top member apertures providing a greater surface area opening therein than said back member apertures whereby said back member presents a greater resistance to convection air current into said cartridge than said top member; and,
    f. A plurality of fragrance pellets contained in said cartridge and positioned between said top and back members.

14. The fragrance device of claim 13 wherein said apertures in said top and back members each comprise an inner array of radial extending air flow slots and an outer array of radial extending air flow slots.

15. The fragrance device of claim 14 wherein said cartridge is generally circular shaped.

16. An improved fragrance device, comprising:
   a. A housing;
   b. An electrically energized means, responsive to incident light, for establishing an air stream through said housing;
   c. A fragrance emitting means positioned in said air stream;
   d. Said electrically energized means including a battery, an electric motor, and a control circuit means for coupling the battery to the motor, said control circuit means including a photo-conductive device;
   e. A light capturing body for aiming at and capturing light from an artificial light source and for directing said captured light at said photo conductive device for energizing said motor;
   f. Means mounting said light capturing body to said housing for manual adjustment of said light capturing body in at least two mutually perpendicular planes;
   g. said light capturing body including a light channel and an inlet aperture for said light channel, said photo-conductive device positioned in said light channel;
   h. said light capturing body configured for selectively capturing light from an artificial light source of limited dimensions and for screening out extraneous light; and,
   i. Said light capturing body and said housing having ball and socket configurations respectively which provide a friction fit therebetween for adjusting said light capturing body in said mutually perpendicular planes.

17. The improved fragrance device of claim 16 wherein said light capturing body includes a segment thereof having a spherically shaped outer surface, said housing body includes a segment thereof having a spherically shaped surface, and said segments are positioned in sliding engagement and dimensioned for providing a friction fit therebetween, whereby said light capturing body is adjustable in at least two mutually perpendicular directions and retains its orientation at a selected adjustment.

18. An improved forced air fragrance device adapted to limit convection flow through the device, comprising:
   a. A housing;
   b. Said housing having a base member and a top member;
   c. Said top member having an aperture formed therein and supporting a fragrance cartridge which forms an apetured closure for said device;
   d. Said cartridge having an inner top member, an outer back member and a plurality of fragrant pellets contained therein;
   e. Said cartridge top and back members each having apertures formed therein to provide for both convection and forced air flow through said cartridge;
   f. said apertures in each of said cartridge top and back members arranged in a first inner array formed near a center of each of said members and a second outer array radially displaced from said inner array and extending circumferentially about said members;
   g. An electrically energized means for establishing a forced air stream through said cartridge apertures; and,
   h. Said electrically energized means including an impeller positioned adjacent said cartridge inner rear member for establishing an air stream through said cartridge which flows inwardly through said cartridge first array of apertures to the interior of said housing, and, outwardly through said cartridge from said housing through said second outer array of apertures.

19. The fragrance device of claim 18 wherein said first array of apertures in said cartridge top and back members each comprises radially extending air flow slots and said second array of apertures comprises radially extending air flow slots.

20. The fragrance device of claim 19 wherein the apertures in said cartridge top member provide a greater surface area opening then the apertures in said cartridge back member.

21. The fragrance device of claim 20 wherein said cartridge is generally circular shaped.

* * * * *